US00PP23125P2

(12) United States Plant Patent
Sheehan

(10) Patent No.: US PP23,125 P2
(45) Date of Patent: Oct. 23, 2012

(54) GRAPEVINE 'SHEEGENE-20'

(50) Latin Name: *Vitis vinifera*
Varietal Denomination: Sheegene-20

(75) Inventor: Timothy P. Sheehan, Vancouver, WA (US)

(73) Assignee: Sheehan Genetics, LLC, Portervile, CA (US)

( * ) Notice: Subject to any disclaimer, the term of this patent is extended or adjusted under 35 U.S.C. 154(b) by 0 days.

(21) Appl. No.: 13/135,332

(22) Filed: Jul. 1, 2011

(51) Int. Cl.
*A01H 5/00* (2006.01)

(52) U.S. Cl. ..... Plt./205

(58) Field of Classification Search ..... Plt./205
See application file for complete search history.

*Primary Examiner* — Annette Para

(74) *Attorney, Agent, or Firm* — Baker Manock & Jensen, PC; Eric C. Cole, Esq.

(57) ABSTRACT

A new and distinct variety of grapevine characterized by the production of medium to large, red-colored seedless grapes that mature in late September, approximately nine weeks later than 'Flame Seedless' (unpatented) when grown in the San Joaquin Valley of Central California. The grapes of this new variety are produced on strong woody stems and branches and are well adapted to commercial handling.

1 Drawing Sheet

Latin name of the genus and species of the plant claimed: The claimed plant relates to a new and distinct variety of *Vitis vinifera* to be known as 'Sheegene-20'.

Variety denomination: The new variety of *Vitis vinifera* is the result of hybridization of 'Princess' (unpatented), the pollen parent, and 'Red Globe' (U.S. Plant Pat. No. 4,787), the seed parent. The new variety was first hybridized by Timothy P. Sheehan in the spring of 2000. The new variety was asexually propagated in the dormant season of 2003, grafted on one hundred seventy-two vines of 'Freedom' virus-free grape rootstock near Fresno, Calif. The new variety was planted in a *Vitis vinifera* variety block located near Fresno, Calif., on the north side of Muscat Avenue approximately five miles east of State Route 145. The new variety produces a medium-large, red-colored seedless grape with good flavor. The new variety has been shown to maintain its distinguishing characteristics through asexual propagation.

CROSS REFERENCE TO RELATED APPLICATIONS

The claimed plant is not subject of a related application.

STATEMENT OF ANY FEDERALLY-SPONSORED RESEARCH AND DEVELOPMENT

The claimed plant is not subject of Federally-sponsored research or development.

BACKGROUND OF THE INVENTION

The present invention relates to a new and distinct variety of grapevine that produces a medium-large, red-colored seedless grape that matures during late September when grown in the San Joaquin Valley of Central California. The new invention resembles 'Flame Seedless' (unpatented).

SUMMARY OF THE INVENTION

The 'Sheegene-20' grapevine is characterized by producing a medium-large, red-colored seedless grape that good flavor and it is productive and mature for harvesting and shipment in late September when grown in the San Joaquin Valley of Central California. The new variety can be compared to 'Flame Seedless' (unpatented) but the grapes produced by the new variety mature approximately nine weeks later, among other distinguishing characteristics.

BRIEF DESCRIPTION OF THE DRAWINGS

The accompanying drawing is a color photograph that displays leaves along the left side, leaves with tendrils along the right side, clusters of the immature and mature grapes in the center, and on the bottom two grapes cut in half displaying the color of the flesh and the shape of the berries.

DETAILED BOTANICAL DESCRIPTION

Referring more to the horticultural description of the new and distinct variety of grapevine, the following has been observed under the ecological conditions prevailing at the origin vineyard located near Fresno, Calif., in the San Joaquin Valley of Central California. All major color descriptions are by reference to the Dictionary of Color by Maerz & Paul, First Edition, published in 1930. Common colors names are also used in several instances.

Vine:

*Size*.—Medium to large for two-year old vine.
*Vigor*.—Very good.
*Chilling requirements*.—Normal for grapevines in the San Joaquin Valley of Central California.
*Figure*.—Wide cordons forming a "T" shape figure.
*Production capacity*.—Very good.
*Regularity of bearing*.—Regular.

Trunk:

*Size*.—Medium to large; 4½ inches [11.43 cm] in circumference, 15 inches [38.10 cm] above graft.
*Surface texture*.—Rough, shaggy.
*Color of bark*.—Pl.7 H10 Piccadilly, Mauvewood +.
*Mature cane color*.—Pl.7 H9 Liver Brown and Autumn Oak.

*Nodes*.—Three nodes on canes.
*Length between nodes*.—3 to 4 inches [7.62 to 10.16 cm].
*Lenticel numbers*.—None.
*Shoot length*.—17 to 32 inches [43.18 to 81.28 cm].
*Shoot shape*.—Contour drooping.
*Tendrils numbers*.—Single at nodes.
*Tendrils size*.—Large; 5½ to 8¼ inches [13.97 to 20.96 cm].
*Tendrils form*.—Bifurcate.
*Tendrils texture*.—Firm.
*Bud shape*.—Triangular.
*Bud size*.—0.02 inches [6 mm] in width, 0.03 inches [8 mm] in length.

Branches:
*Size*.—Medium to large; 6 inches [15.24 cm] in circumference.
*Cordons*.—32 to 35 inches from trunk (81.28 to 88.90 cm).
*Surface texture*.—Slightly rough with groove.
*Color* (*one year or older wood*).—Pl.7 H9 Liver Brown+Autumn Oak.
*Color* (*immature branches*).—Pl.19 K6 Sea gr. on lower side of branch; Pl.52 L8 *Cineraria* on upper side of branch.

Leaves:
*Size*.—Medium to large.
*Density*.—Dense.
*Average length*.—4.72 inches [11.99 cm].
*Average width*.—6.89 to 7.09 inches [17.50 to 18.01 cm].
*Form*.—Pentagonal.
*Texture* (*upper surface*).—Smooth.
*Texture* (*lower surface*).—Slightly glabrous.
*Color* (*upward disposed surface*).—Pl.23 J9 Mt. Vernon gr.
*Color* (*downward disposed surface*).—Pl.21 L7 Med. Dark gr.
*Leaf vein color*.—Pl.17 L7 Viridine Y.
*Marginal form*.—Slightly undulated.
*Leaf vein thickness*.—0.008 inches [2 mm].
*Leaf margin*.—Toothed.
*Glandular characteristics*.—None.
*Petiole size*.—Large.
*Petiole length*.—4.53 to 5.12 inches [11.51 to 13.00 cm].
*Petiole color* (*lower surface*).—Pl.20 L8 Near Eden gr.
*Petiole color* (*upper surface*).—Pl.16 L8 Dark Cardinal.
*Petiole sinus form*.—Upside down 'U' shape.
*Lobe* (*average*).—Four.
*Tooth number*.—Four to six.
*Tooth shape*.—Triangular.

Inflorescence:
*Size*.—6.70 to 7.50 inches [17.02 to 19.05 cm].
*Number per spur*.—Two to three.
*Number per vine*.—Many; up to sixty-four.
*Quantity*.—Proficient.

Flowers:
*Flower buds*.—Small; 0.04 to 0.08 inches [1 to 2 mm].
*Flower buds surface*.—Glabrous.
*Flower buds*.—Generally hoary.
*Date of bloom*.—May 9, 2010.
*Date of full bloom*.—May 12, 2010.
*Size*.—0.16 inches [4 mm].
*Petals* (*color*).—Pl.18 J7 Spring gr.
*Petals* (*size*).—Small; 0.08 inches [2 mm].
*Pistil color*.—Pl.17 L8 Neva gr.
*Date of visible berry set*.—May 12, 2010.
*Size of berries*.—Small; 0.08 inches [2 mm].

Fruit:
*Solids*.—19.2 Brix.
*Acids*.—0.45.
*Sugar/acid ratio*.—42.6.
*Juice pH*.—3.32.
*Seeds*.—None.
*Capstem pedicel*.—0.24 to 0.35 inches [6 to 9 mm].
*Berry weight*.—11.36 grams.
*Juice color*.—Pl.13 L4 Near Bistre gr.
*Cluster size*.—Medium to large.
*Cluster average length* (*not including stem*).—7.31 inches [18.57 cm].
*Cluster average diameter*.—4.82 inches [12.24 cm].
*Cluster average weight*.—1 lbs. 2 oz. [511.2 grams].
*Compactness*.—Compact.
*Cluster form*.—Conical.
*Stem* (*generally*).—2.17 inches [5.51 cm].
*Stem* (*caliper*).—0.16 to 0.24 inches [4 to 6 mm].
*Berry size*.—Medium to large.
*Berry form*.—Ovate.
*Berry numbers*.—45 to 75 berries per bunch.
*Berry size* (*average dimension along longitudinal axis*) .—0.98 to 1.26 inches [2.49 to 3.20 cm].
*Berry size* (*average dimension along transverse axis*).—0.79 to 0.87 inches [20 to 22 mm].

Skin:
*Skin thickness*.—Medium.
*Texture*.—Tough.
*Tendency to crack*.—None.
*Blush color*.—Pl.55 L7 Near Rubient.
*Ground color*.—Pl.12 L1; Oil Y.
*Pulp*.—Near Pl.13 K3 Olive gr.
*Lenticels*.—None.

Flesh:
*Flesh color*.—Pl.12 K3 Olive gr.
*Juice production*.—Good.
*Flavor*.—Very good.
*Aroma*.—Mild.
*Texture*.—Firm.
*Ripening*.—Even.
*Eating quality*.—Very good.
*Use*.—Fresh Market.
*Resistance to disease*.—Uknown.
*Harvesting*.—Late August in the San Joaquin Valley of Central California.
*Shipping and handling qualities*.—Good.

Having thus described and illustrated our new variety of grapevine, I claim:

1. A new variety of grapevine to be known as 'Sheegene-20' and parts thereof, substantially as illustrated and described, characterized principally by its production of medium to large, red-colored seedless grapes that mature later in the season of ripening than does 'Flame Seedless' (unpatented) that it resembles.

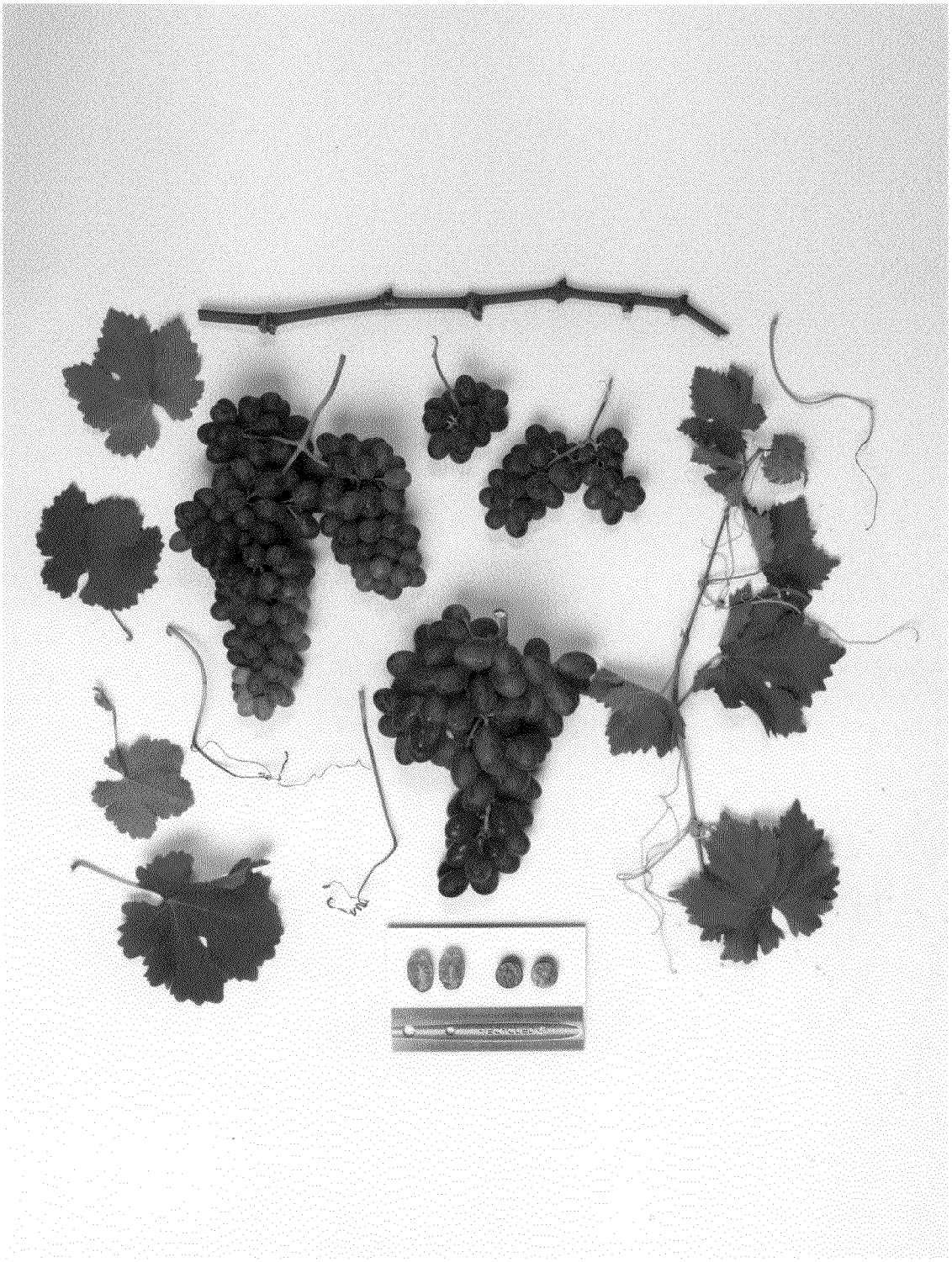

* * * * *